(12) United States Patent
Sharifi-Mehr et al.

(10) Patent No.: US 12,064,124 B2
(45) Date of Patent: Aug. 20, 2024

(54) TOOLS FOR INSERTION OF A SPINAL IMPLANT AND METHODS OF USING SAME

(71) Applicant: K2M, Inc., Leesburg, VA (US)

(72) Inventors: Amir Ali Sharifi-Mehr, Bloomingdale, NJ (US); Oliver Buchert, Franklin Lakes, NJ (US); Larry Hazbun, Davie, FL (US); Matthew J. Mcgirt, Charlotte, NC (US); David Okonkwo, Wexford, PA (US)

(73) Assignee: K2M, Inc., Leesburg, VA (US)

( * ) Notice: Subject to any disclaimer, the term of this patent is extended or adjusted under 35 U.S.C. 154(b) by 147 days.

(21) Appl. No.: 17/950,677

(22) Filed: Sep. 22, 2022

(65) Prior Publication Data
US 2023/0017664 A1    Jan. 19, 2023

Related U.S. Application Data

(62) Division of application No. 17/060,823, filed on Oct. 1, 2020, now Pat. No. 11,559,315.

(60) Provisional application No. 62/910,662, filed on Oct. 4, 2019.

(51) Int. Cl.
| | |
|---|---|
| *A61B 17/17* | (2006.01) |
| *A61B 17/16* | (2006.01) |
| *A61B 17/34* | (2006.01) |
| *A61B 34/30* | (2016.01) |
| *A61B 34/00* | (2016.01) |
| *A61B 34/32* | (2016.01) |

(52) U.S. Cl.
CPC ...... *A61B 17/1617* (2013.01); *A61B 17/1757* (2013.01); *A61B 17/3496* (2013.01); *A61B 34/30* (2016.02); *A61B 34/32* (2016.02); *A61B 34/76* (2016.02)

(58) Field of Classification Search
CPC .............. A61B 17/1617; A61B 17/1757
See application file for complete search history.

(56) References Cited

U.S. PATENT DOCUMENTS

| | | | |
|---|---|---|---|
| 5,320,115 A * | 6/1994 | Kenna | A61B 17/1675 128/898 |
| 8,010,180 B2 | 8/2011 | Quaid et al. | |
| 9,002,426 B2 | 4/2015 | Quaid et al. | |
| 9,119,655 B2 | 9/2015 | Bowling et al. | |
| 9,566,122 B2 | 2/2017 | Bowling et al. | |
| 10,028,788 B2 | 7/2018 | Kang | |
| 10,070,928 B2 | 9/2018 | Frank et al. | |
| 10,098,704 B2 | 10/2018 | Bowling et al. | |
| 10,117,713 B2 | 11/2018 | Moctezuma De La Barrera et al. | |
| 10,166,109 B2 | 1/2019 | Ferko | |
| 10,357,257 B2 | 7/2019 | Kostrzewski | |

(Continued)

OTHER PUBLICATIONS

Partial European Search Report for EP20199708.7 issued Apr. 9, 2021; 5 pages.

*Primary Examiner* — Christian A Sevilla
(74) *Attorney, Agent, or Firm* — Lerner David LLP

(57) ABSTRACT

A surgical tool for use with a drill bit to prevent skiving at an implant insertion site on a bone includes a cannulated sleeve having a distal end defining a burr surface. The distal end may be detachable from a body of the cannulated sleeve. The tool may be used with more than one distal end, each of the distal ends defining a burr surface having a different cutting surface from the others. The tool may form a system that includes the drill bit.

20 Claims, 19 Drawing Sheets

(56) References Cited

U.S. PATENT DOCUMENTS

| | | |
|---|---|---|
| 10,765,438 B2 | 9/2020 | Kostrzewski |
| 10,945,742 B2 | 3/2021 | Kostrzewski |
| 2006/0079908 A1* | 4/2006 | Lieberman ......... A61B 17/1757 606/99 |
| 2006/0142775 A1 | 6/2006 | Heneberry et al. |
| 2008/0140078 A1* | 6/2008 | Nelson ............... A61B 17/1642 606/80 |
| 2011/0152866 A1* | 6/2011 | Knutson ............ A61B 17/3472 606/86 R |
| 2014/0180290 A1 | 6/2014 | Otto et al. |
| 2015/0119987 A1 | 4/2015 | Davignon et al. |
| 2017/0128136 A1 | 5/2017 | Post |
| 2018/0168750 A1 | 6/2018 | Staunton et al. |
| 2018/0325608 A1 | 11/2018 | Kang et al. |
| 2019/0083271 A1* | 3/2019 | Donner .............. A61B 17/1739 |
| 2019/0142407 A1 | 5/2019 | Jung et al. |

\* cited by examiner

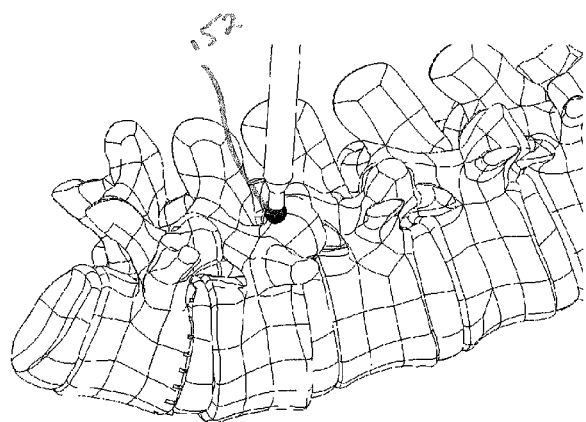
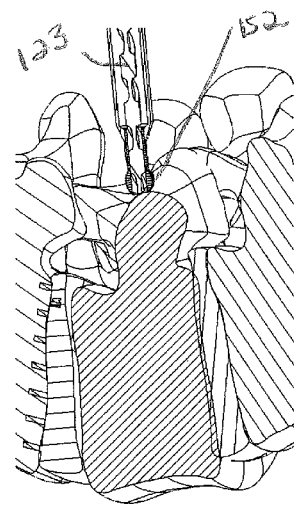
Fig. 9A        Fig. 9B
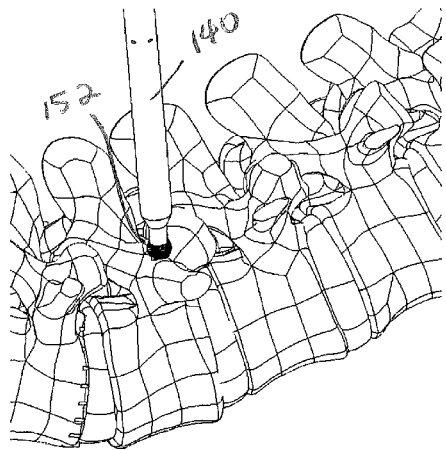
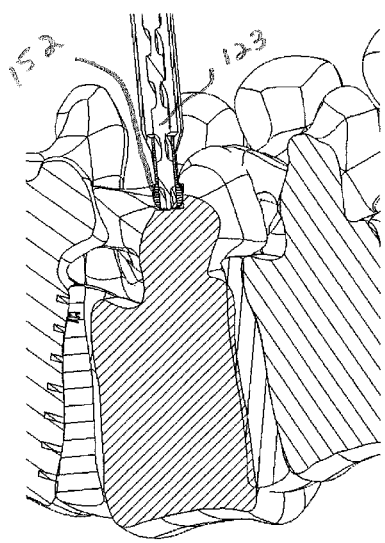
Fig. 10A        Fig. 10B

TOOLS FOR INSERTION OF A SPINAL IMPLANT AND METHODS OF USING SAME

CROSS-REFERENCE TO RELATED APPLICATIONS

This application is a divisional of U.S. patent application Ser. No. 17/060,823, filed on Oct. 1, 2020, which claims the benefit of the filing date of U.S. Provisional Patent Application No. 62/910,662 filed Oct. 4, 2019, the disclosures of which are hereby incorporated herein by reference.

BACKGROUND OF THE INVENTION

The present invention generally relates to instrumentation for forming an opening in bone for receiving an implant, and more particularly for forming an opening in a pedicle of a vertebra.

A technique commonly referred to as spinal fixation is employed for fusing together and/or mechanically immobilizing vertebrae of the spine. Spinal fixation may also be used to alter the alignment of adjacent vertebrae relative to one another so as to change the overall alignment of the spine. Such techniques have been used effectively to treat many degenerative conditions and, in most cases, to relive pain suffered by the patient.

In some applications, a surgeon will install implants, such as pedicle screws, into the pedicles of adjacent vertebrae (along one or multiple levels of the spine) and thereafter connect the screws with a spinal rod in order to immobilize and stabilize the vertebral column. Whether conducted in conjunction with interbody fusion or across single or multiple levels of the spine, the use of pedicle screws connected by fixation rods is an important treatment method employed by surgeons.

Prior to implantation of the implant, the target area, e.g. the pedicle, is incised to create an opening for receiving the implant. One problem a surgeon or other medical professional may face while creating such an incision within bone is skiving due to the shape and anatomy of the bone that is often angled with respect to the axis along which the instrumentation and implant are used. When the incision tool slips along a surface of the bone, the trajectory of the tool and the resulting opening becomes inaccurate for the placement of the implant.

There remains room for improvement in the design and use of instrumentation that prevents skiving which provides for surgical efficiency and maintains safety and accuracy for implanting an implant along a desired trajectory.

BRIEF SUMMARY OF THE INVENTION

A first aspect of the present disclosure includes a surgical tool for use with a drill bit to prevent skiving at an implant insertion site on a bone, the tool includes a cannulated sleeve having a distal end defining a burr surface.

In other embodiments, the burr surface may be annular. The burr surface may be bulbous. The distal end and the cannulated sleeve may be of a single monolithic construction. The distal end may be detachable from the cannulated sleeve. The tool may be part of a kit that includes more than one distal end, each of the distal ends may define a burr surface having a different cutting surface from the others. The tool may be part of a system to prevent skiving at an implant insertion site on a bone that also includes a drill bit configured to be disposed within the cannulated sleeve. In a first configuration the cannulated sleeve and the drill bit may be rotationally coupled to each other and in a second configuration the cannulated sleeve and the drill bit may rotate independent of one another. The cannulated sleeve may have a lock at the proximal end of the cannulated sleeve to axially and rotationally couple the cannulated sleeve and the drill bit. The system be configured to be actuated by a robotic end effector. The distal end of the cannulated sleeve may define an opening.

A second aspect of the present disclosure includes a surgical system for use with a drill bit to prevent skiving at an implant insertion site on a bone, the system including a cannulated guide tube, an obturator configured to be disposed within the guide tube, and a burr tool configured to be disposed within the obturator, the burr tool having a distal end defining a burr surface.

In other embodiments, the guide tube, obturator, and burr tool may be coaxial when the obturator is positioned in the guide tube and the burr tool is positioned in the obturator. The burr tool may be configured to be spring-loaded into the obturator. The system may include a drill bit configured to be disposed within the guide tube.

Another aspect of the present disclosure includes a method of preparing an implant insertion site on a bone, the method including advancing a surgical system along an insertion axis, the system including a cannulated sleeve having a burr surface at a distal end and a drill bit disposed within the cannulated sleeve; and rotating the cannulated sleeve about the insertion axis to cause the burr surface to contact a surface of the bone that is not perpendicular to the insertion axis to form a pocket in the bone.

In other embodiments, the method may include drilling a hole into the bone at the pocket by rotating the drill bit. The method may include the step of rotationally coupling the cannulated burr sleeve and the drill bit with a lock. The method may include the step of retracting the cannulated sleeve. The method may include the step of disengaging the lock and retracting the cannulated sleeve relative to the drill bit. The pocket formed may have a substantially rounded surface.

Yet another aspect of the present disclosure includes a method of preparing an implant insertion site on a bone, the method including advancing a surgical system along an insertion axis, the system including a burr tool positioned within an obturator, the obturator positioned within a guide tube, and rotating the burr tool about the insertion axis to cause a distal burr surface of the burr tool to contact a surface of the bone that is not perpendicular to the insertion axis to form a pocket in the bone.

In other embodiments, the method may include the step of retracting the obturator and the burr tool from the guide tube. The method include the step of inserting a drill within the guide tube. The method may include the step of drilling a hole into the bone at the pocket by rotating the drill bit.

BRIEF DESCRIPTION OF THE DRAWINGS

FIGS. 9A and 9B are schematic and cross-sectional views, respectively, of the system of FIG. 1 positioned above the desired trajectory of the pedicle.

FIGS. 10A and 10B are schematic and cross-sectional views, respectively, of the system of FIG. 1 cutting into the pedicle;

DETAILED DESCRIPTION

Figure 1:
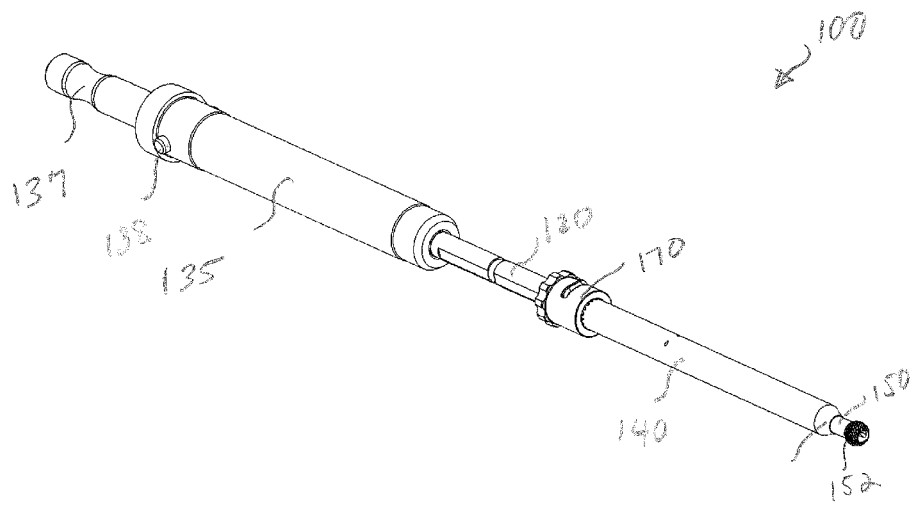
FIG. 1 is a perspective side view of a system including a burr sleeve in conjunction with a drill in accordance with a first aspect of the present disclosure.

The present invention generally relates to cutting tools used for forming an opening for an implant during surgery. The cutting tools are designed to advantageously minimize or prevent skiving or slipping along a surface of the bone. This provides of the advantage of efficiently forming an accurately placed cannulation along a desired trajectory. Those of skill in the art will recognize that the following description is merely illustrative of the principles of the invention, which may be applied in various ways to provide many different alternative embodiments.

In describing certain aspects of the present inventions, specific terminology will be used for the sake of clarity. However, the inventions are not intended to be limited to any specific terms used herein, and it is to be understood that each specific term includes all technical equivalents, which operate in a similar manner to accomplish a similar purpose. In the drawings and in the description which follows, the term "proximal" refers to the end of the fixation members and instrumentation, or portion thereof, which is closest to the operator in use, while the term "distal" refers to the end of the fixation members and instrumentation, or portion thereof, which is farthest from the operator in use.

System 100 is designed to facilitate co-axial burring and drilling of a target location of bone. The system forms a landing zone on the surface of the bone, e.g. a pedicle of a vertebra, to prevent the subsequent drill from skiving during hole preparation during surgery, e.g. spinal surgery. Although described herein with reference to a burr surface, the disclosure contemplates any cutting feature capable of producing side cutting action, and the cutting geometry of the surface is not limited to a burr so long as this function is achieved.

Figure 8:
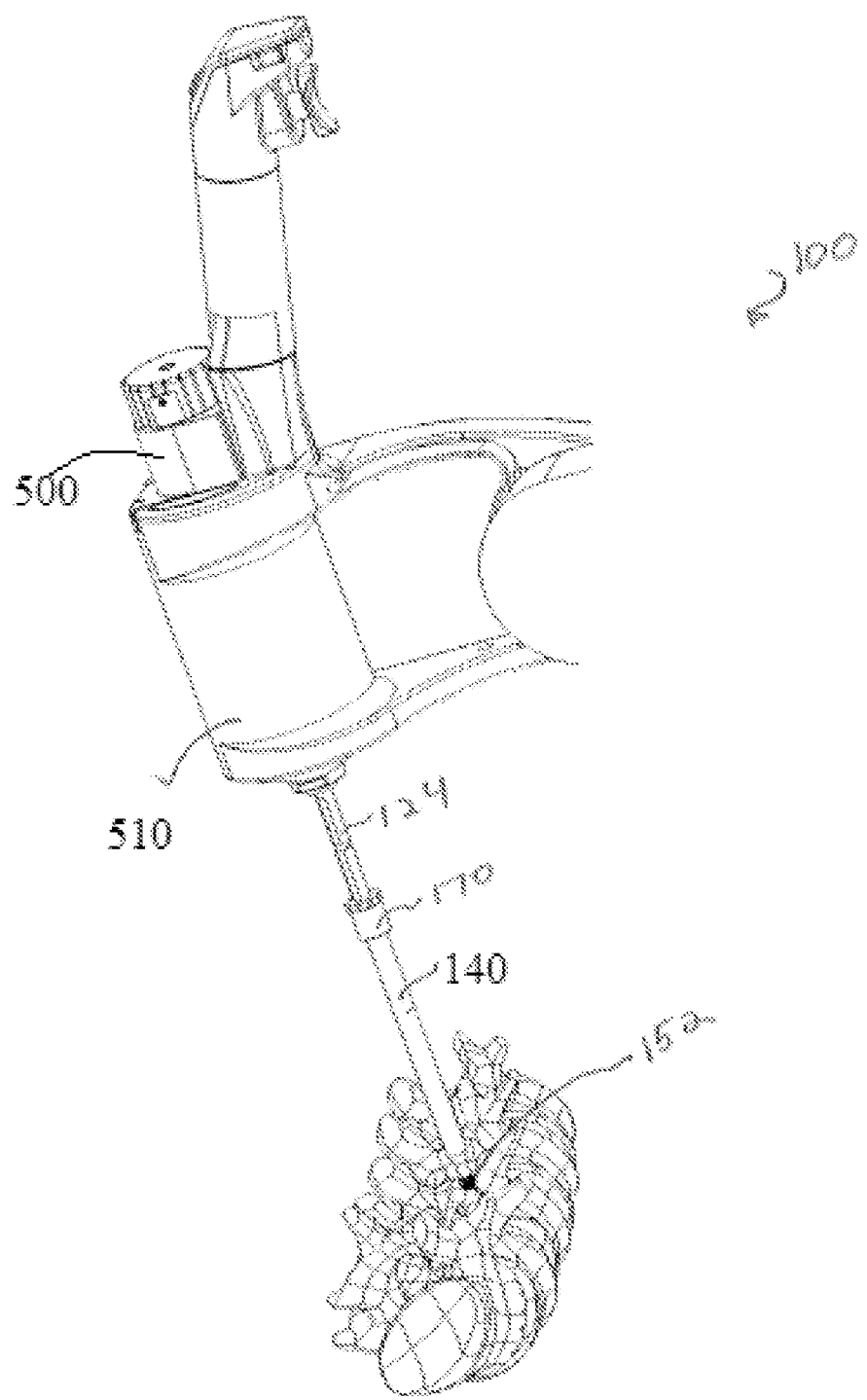
FIG. 8 is a schematic view of a robotic device and the system of FIG. 1 in conjunction with a pedicle, in accordance with an aspect of the present disclosure.

System 100 includes an inner drill bit 124 and an outer cannulated sleeve 140 securable to drill bit 124 such that at least a portion of drill bit is positionable through sleeve 140, as discussed in further detail below. At a proximal end of system 100, a drive body 135 is connected to a drill bit 124. Drive body 135 is rotatably coupled to drill bit 124 so that drive body 135 and drill bit 124 rotate in the same direction. A proximal end 137 of drive body 135 attaches to a robotic end effector 510 of a robotic device 500, as shown in FIG. 8. Robotic end effector 510 transmits torque via cross pin 138 to rotate drive body 135 and thus drill bit 124.

Drill bit 124 extends along a longitudinal axis from a proximal end 125 to a distal end 128 thereof. Drill bit 124 includes a tapered region 129 which transitions to a cutting portion 123 at distal end 128 of drill bit 124. Cutting portion 123 has a smaller width than the proximal portion of the drill bit 124, measured in a direction perpendicular to the longitudinal axis of the drill bit. In other examples, the drill bit 124 may be another known cutting tool such as a reamer.

Figure 5:
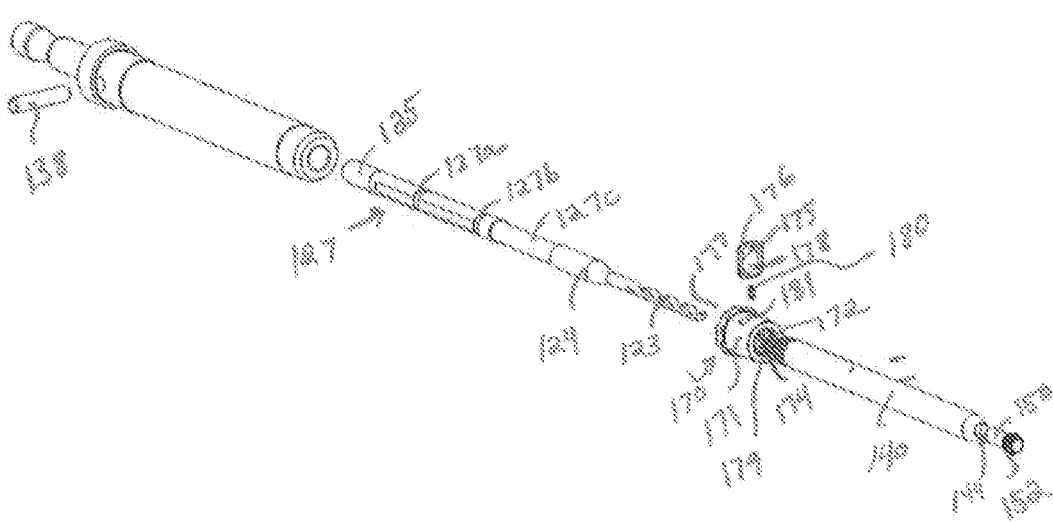
FIG. 5 is an exploded view of the system of FIG. 1.

As shown in FIG. 5, drill bit 124 includes a proximal portion 127 which is keyed along a portion of its length to rotationally lock the drill bit relative to sleeve 140. Proximal portion 127 includes reduced diameter segments 127a, 127b, and 127c spaced apart along the axis of drill bit 124 for connecting drill bit 124 with sleeve 140, described in further detail below.

Cannulated sleeve 140 is designed to be releasably locked to drill bit 124. Sleeve 140 extends along a longitudinal axis from a proximal end 145 to a distal end 148. Cannulated sleeve 140 has a body with a substantially cylindrical shape. As shown in FIG. 5, cannulated burr extension 150 attaches to distal end 148 of sleeve 140 and defines a passageway co-axial with a passageway 144 of sleeve 140 such that burr extension 150 and sleeve 140 form a continuous passageway. Alternatively, burr extension 150 and sleeve 140 may be constructed as a single, monolithic piece.

Figure 6A:
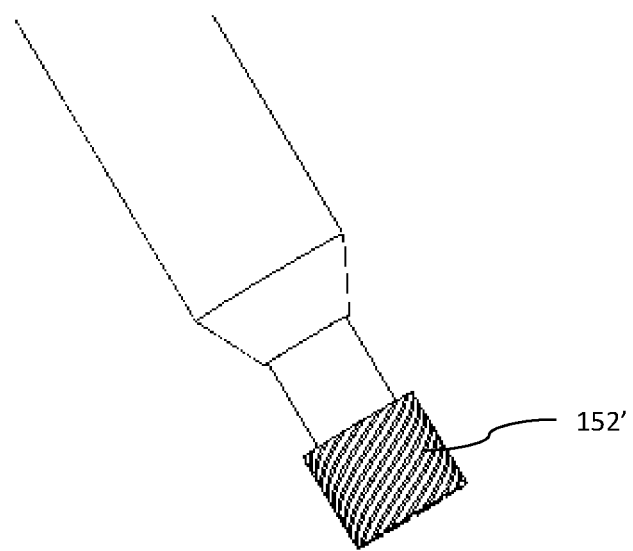
FIGS. 6A and 6B are a perspective side view and a cross-sectional view, respectively, of a burr sleeve according to an alternative embodiment of the present disclosure.
Figure 6B:
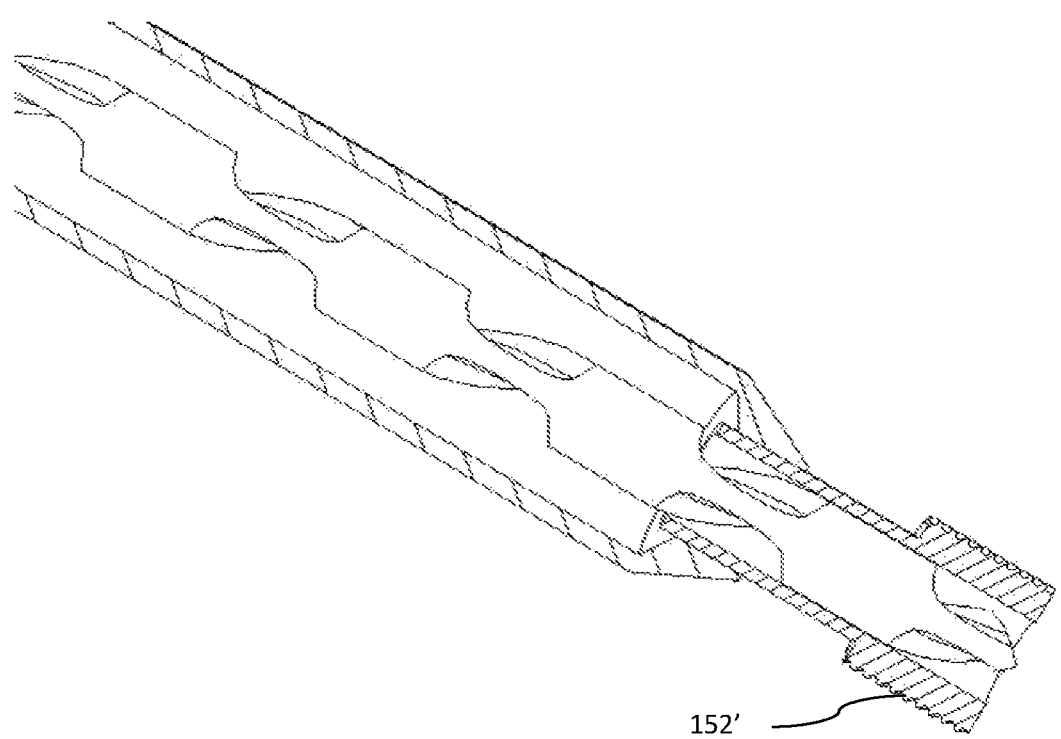

Burr extension 150 defines an annular distal outer burr surface 152 in the form of a burr. Outer burr surface 152 has a bulbous, rounded shape for finely cutting into bone. Burr surface 152 is a cutting surface for forming a pocket in the bone. The rounded portion and/or the distal edge include cutting features to cut into bone. The spherical shape of the outer burr surface 152 allows the burr to cut into an angled surface to cut a pocket in the pedicle by allowing for side cutting and partial front cutting. In instances in which the bone surface is at an angle of about 30-55 degrees, particularly, about 40-45 degrees, the burr surface is particularly advantageous to clear the material on the side. Although the illustrated embodiment shows outer burr surface 152 as spherical, the outer burr surface 152' may instead be cylindrical, as shown in FIGS. 6A and 6B. Further, the outer diameter of burr surface 152 is greater than a maximum diameter of the cutting portion 123 of drill bit 124. Therefore, even if the burr sleeve were to experience slight skiving, because the diameter of the burr sleeve is larger than the drill bit, the pocket would still be large enough to create a surface for the drill bit to cut into without the drill bit skiving. Additionally, the outer diameter of burr surface 152 may be equal to or greater than a maximum diameter of the tulip head of the pedicle screw implant, as described in greater detail below.

Figure 3:
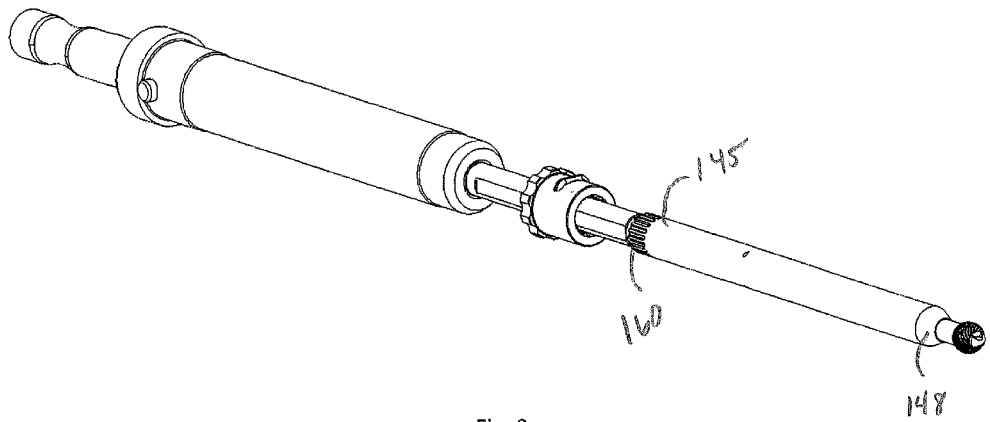
FIGS. 3 and 4 are alternative perspective side views of the system of FIG. 1.

Sleeve 140 defines passageway 144 extending through its entire length so that sleeve 140 is sized and shaped to receive drill bit 124. As shown in FIG. 3, proximal end 145 of sleeve 140 includes a spline member 160 extending around the circumference of sleeve 140 and having splines that extend in a direction parallel to the longitudinal axis of sleeve 140 to engage a corresponding internal spline member 179 a on lock assembly 170.

Figure 2:
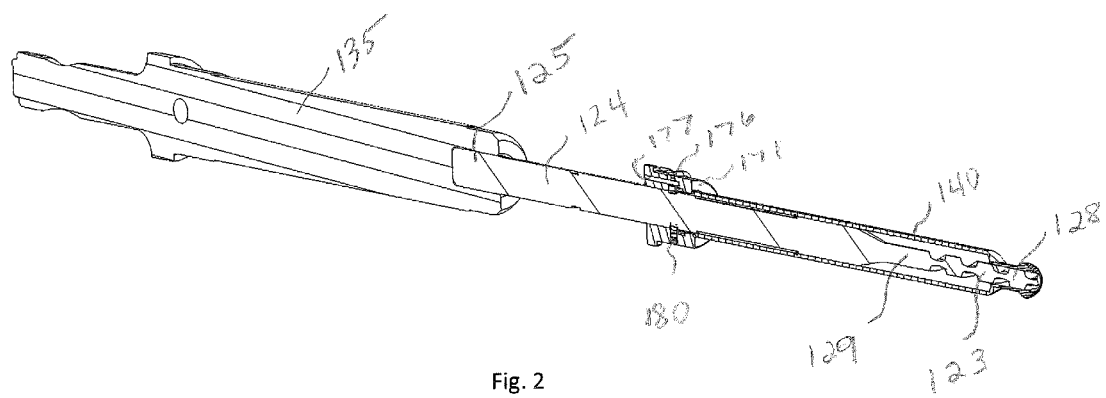
FIG. 2 is a cross-sectional view of the system of FIG. 1.

As shown in FIG. 5, lock assembly 170 includes an outer tubular member 171 which has a substantially cylindrical shape and includes an interior surface 172 defining a passageway 174 for receiving sleeve 140 and drill bit 124. Interior surface 172 includes spline member 179 for mating with and engaging spline member 160 of sleeve 140 to rotationally couple sleeve 140 and outer tubular member 171. A slot 181 extends through an outer surface and interior surface 172 of outer tubular member 171. A button 176 is received within slot 181 and has a generally rectangular shape having two opposing rounded upper and lower surfaces. Button 176 includes a hole 175 for receiving a pin 177 therethrough to secure button 176 to tubular member 171, as tubular member 171 includes an opening for receiving pin 177, as shown in FIG. 2.

Button 176 further defines through-opening 178 for receiving drill bit 124. In a rest condition, button 176 is biased by a spring 180 so that spring 180 maintains secure engagement with drill bit 124. As shown in FIG. 2, button 176 engages a reduced diameter segment 127*b* of drill bit 124 to lock drill bit 124 relative to lock assembly 170 and to sleeve 140. Thus, in a first configuration, with lock assembly 170 engaged, cannulated sleeve 140 is rotationally and axially locked with drill bit 124 due to lock assembly 170 and the keyed portions along drill bit 124. In an actuated condition, when button 176 is depressed by a user, spring 180 is compressed and tubular member 171 and sleeve 140 are uncoupled from drill bit 124 such that the sleeve 140 can axially travel and rotate relative to drill bit 124. In this manner, sleeve 140 can be moved together along drill bit 124 to a different location. For example, tubular member 171 can be moved proximally and engage reduced diameter segment 127*a* and axially locked at that location to control the depth of burr surface 152 relative to cutting portion 123 of drill bit 124. This allows drill bit 124 to extend distally of burr surface 152 during drilling. Burr sleeve 140 can rotate relative to drill bit 124 in this retracted position to allow the burr sleeve to act like a tissue sleeve to prevent tissue wrap during the drilling of the hole.

For assembly, burr extension 150 is positioned within cannulated sleeve 140, or alternatively, sleeve 140 may be pre-assembled with burr extension 150. However, in some instances, it may be desirable to change the diameter of the burr surface, so burr extension 150 and cannulated sleeve 140 may be manufactured and sold as two pieces such that the appropriate size of burr extension 150 may be chosen based on the needs of the surgical procedure. Thus, an aspect of the present disclosure is a kit including cannulated sleeve 140 and at least one burr extension 150. The kit may include a plurality of burr extensions 150 having different diameters and differentiated cutting surfaces to accommodate the needs of the surgical procedure. The kit may include lock assembly 170 and/or drill 140.

With burr extension 150 and cannulated sleeve 140 attached so as to operate as a single integral construct, cannulated sleeve 140 is engaged with lock assembly 170. Drill bit 124 is positioned within lock assembly 170 and sleeve 140 and engaged with drive body 135. In an initial configuration, cutting portion 123 of drill bit 124 remains within passageway 144 defined by sleeve 144 and burr extension 150 so that it does not protrude distally of the distal end of burr extension 150. Drive body 135 is loaded into robotic end effector 510, shown in FIG. 8. Actuation of robotic end effector 510 causes rotation of drive body 135 and thus drill bit 124.

Figure 7A:
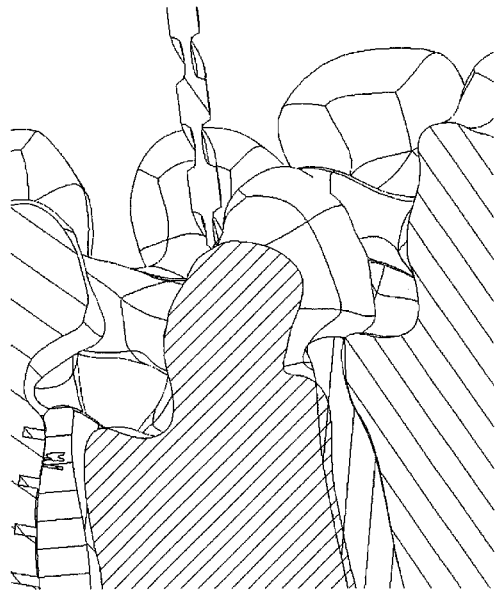
FIGS. 7A and 7B are cross-sectional views of a drill in conjunction with a pedicle, as is known in the prior art.
Figure 7B:
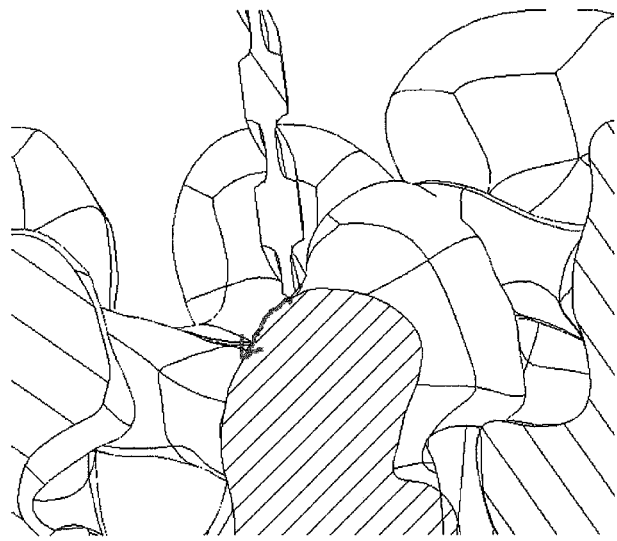

FIGS. 7A and 7B illustrate the difficulties with drilling into the pedicle. As shown, the anatomy of the pedicle includes curved surfaces at the bone interface. As the axial force of the drill is transmitted, the drill may slide down the side of the pedicle, indicated by the arrow in FIG. 7B, resulting in skiving and a loss of the desired trajectory for hole preparation. Skiving results in sacrificed efficiency as well as accuracy.

Figure 11:
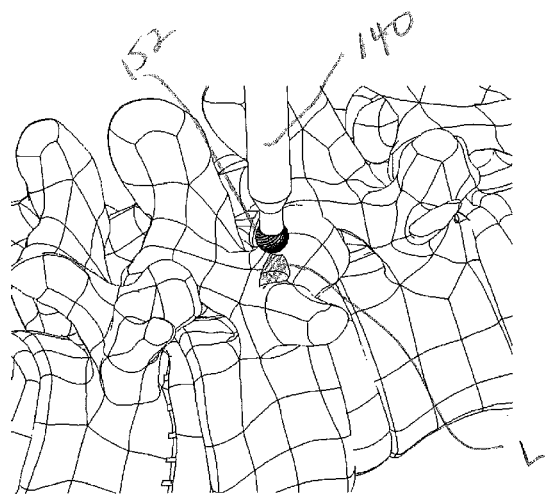
FIG. 11 is a schematic view of the pocket formed by the system of FIG. 1 on the pedicle.
Figure 12:
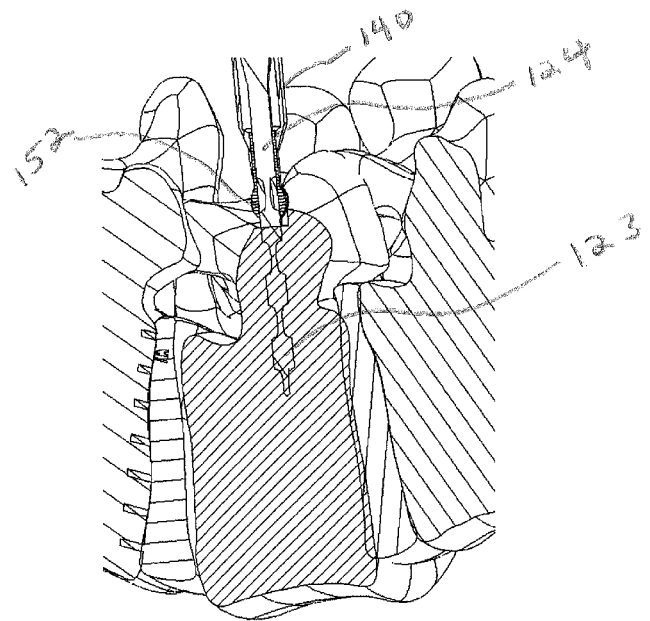
FIG. 12 is a cross-sectional view of the system of FIG. 1 drilling into the pedicle.
Figure 13:
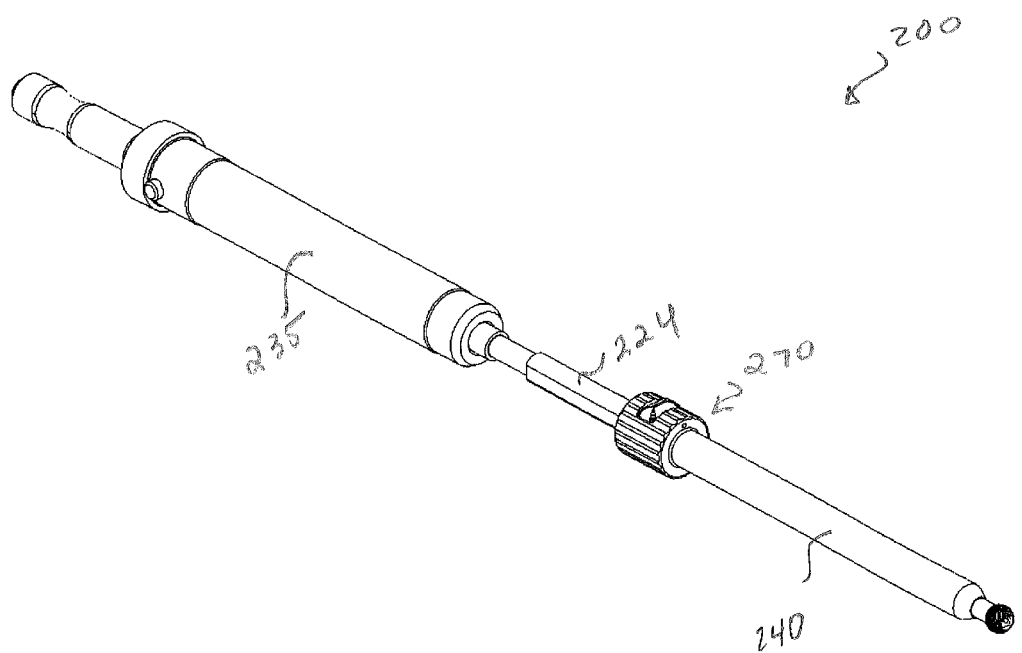
FIG. 13 is a perspective side view of a system in accordance with another aspect of the present disclosure.

In use, system 100 is positioned with outer surface 152 of burr extension above a pedicle, shown in FIGS. 9A and 9B. The robotic end effector 510 is placed on haptic line trajectory and actuated causing burr extension 150 to cut into the surface of the pedicle that is angled or otherwise not perpendicular to the insertion axis, shown in FIGS. 10A and 10B. The placement of sleeve 140 and outer burr surface 152 surrounding drill bit 124 forms a landing zone or shallow pocket within the bone, labeled as "L" in FIG. 11. The landing zone or pocket mimics the shape of the outer burr surface 152. Due to the angle of the trajectory, the burr sleeve produces a side cut on the bone surface. The formed pocket has a maximum width that is larger than a diameter of cutting portion 123 of drill bit 124. Further, the formed pocket may have a maximum width that is equal to or larger than a diameter of the tulip head of the pedicle screw to facilitate proper seating of the tulip head to the desired depth in the bone.

Figure 4:
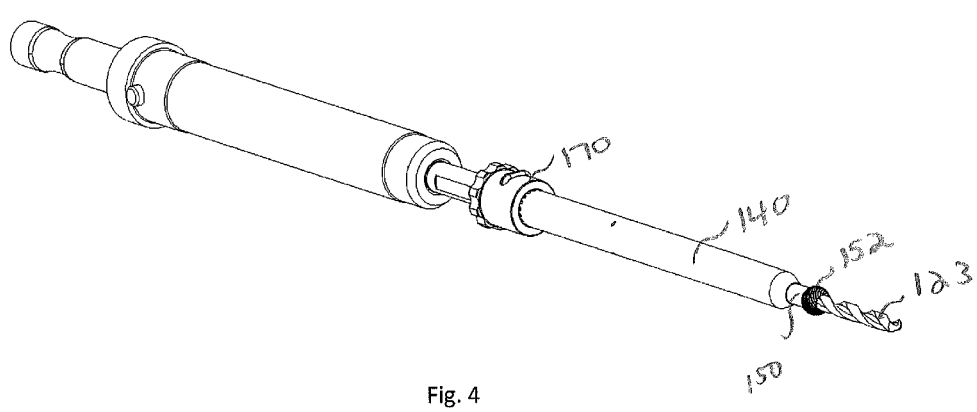

After the pocket "L" is formed, button 176 can be depressed to disengage lock assembly 170 and to uncouple drill bit 124 relative to sleeve 140. Lock assembly 170 and sleeve 140 are translated proximally in a retraction direction, shown between FIGS. 3 and 4. Sleeve 140 and lock assembly 170 can be engaged with reduced segment 127*a* so that cannulated sleeve and thus burr surface 152 is proximal to cutting portion 123 of drill bit 124 to act as a depth stop for burr surface 152. Robotic end effector 510 drives drill bit 124 along the same trajectory and drill bit 124 drives into bone to cannulate the pedicle for implantation of an implant, e.g. pedicle screw. This pocket or landing zone "L" eliminates the skive angle which is normally present for pedicle screw placement and hole preparation, as is shown by the arrow in FIG. 7B making it easier to avoid skiving. As drill bit 124 drills into bone through pocket "L", the spherical shape of outer burr surface 152 creates a rounded, shallow pocket in bone, which facilitates cutting portion 123 to tend to get pulled toward the center of the pocket to prevent skiving. Additionally, during drilling, sleeve 140 may act as a soft tissue sleeve and may continue to surround drill bit 124 to protect the soft tissue as drill bit 124 drills into bone. Further, as discussed above, the pocket created by burr 150 may help to properly seat the tulip head of the pedicle screw, which may be particularly beneficial where a bone anatomy, e.g. a hypertrophied facet, prevents the full diameter of the tulip head from seating to the desired depth.

System 100 may be used with robotic systems during spinal surgery. Robotic systems such as robotic device 500 may be used throughout the pre-operative and intraoperative stages of the surgery. Preoperative planning for surgeries may include determining the bone quality in order to optimize bone preparation. Bone quality information, such as bone density or elastic modulus, can be ascertained from preoperative scans, e.g. CT scans. The bone quality data can be used to determine optimal properties for effective implant engagement. Examples of such methods are found in U.S. Pat. No. 10,166,109 to Ferko, filed on Sep. 18, 2014, entitled "Patient Specific Bone Preparation for Consistent Effective Fixation Feature Engagement," U.S. Patent Application Publication No. 2015/0119987 to Davignon et al., filed on Oct. 28, 2014, entitled "Implant Design Using Heterogeneous Bone Properties and Probabilistic Tools to Determine Optimal Geometries for Fixation Features," and U.S. Pat. No. 10,070,928 to Frank et al., filed on Jul. 1, 2015, entitled "Implant Placement Planning," each of which is hereby incorporated by reference herein in its entirety. In addition to preoperative imaging, robotic surgery techniques may employ imaging, such as fluoroscopy, during surgery. In such cases, systems integrating the surgical system with the imaging technologies facilitate flexible and efficient intraoperative imaging. Exemplary systems are described in U.S. Pat. No. 10,028,788 to Kang, filed on Dec. 31, 2013, entitled "System for Image-Based Robotic Surgery," hereby incorporated by reference herein in its entirety.

Robotic systems and methods may be used in the performance of spine surgeries. In some such instances, robotic systems and methods may be used in the performance of spine surgeries to facilitate the insertion of implants in the patient's spine as in, for example, U.S. Patent Application Publication No. 2018/0325608 to Kang et al., filed on May 10, 2018, entitled "Robotic Spine Surgery System and Methods," the disclosure of which is hereby incorporated by reference herein in its entirety. The robotic system generally includes a manipulator and a navigation system to track a surgical tool relative to a patient's spine. The surgical tool may be manually and/or autonomously controlled. Examples of robotic systems and methods that employ both a manual and a semi-autonomous are described in U.S. Pat. No. 9,566,122 to Bowling et al., filed on Jun. 4, 2015, and entitled "Robotic System and Method for Transitioning Between Operating Modes," and U.S. Pat. No. 9,119,655 to Bowling et al., filed on Aug. 2, 2013, entitled "Surgical Manipulator Capable of Controlling a Surgical Instrument in Multiple Modes," each of which is hereby incorporated by reference herein in its entirety.

A robotic controller may be configured to control the robotic arm to provide haptic feedback to the user via the robotic arm. This haptic feedback helps to constrain or inhibit the surgeon from manually moving the incision tool beyond predefined virtual boundaries associated with the surgical procedure. Such a haptic feedback system and associated haptic objects that define the virtual boundaries are described in, for example, U.S. Pat. No. 9,002,426 to Quaid et al., filed on Jun. 23, 2008, entitled "Haptic Guidance System and Method," and U.S. Pat. No. 8,010,180 to Quaid et al., filed on Dec. 21, 2012, entitled "Systems and Methods for Haptic Control of a Surgical Tool," and U.S. Pat. No. 10,098,704 to Bowling et al., filed on May 18, 2016, entitled "System and Method for Manipulating an Anatomy," each of which is hereby incorporated by reference herein in its entirety.

In some cases of autonomous positioning, a tool center point (TCP) of a surgical tool, such as sleeve 140 and/or drill bit 124 is brought to within a predefined distance of a starting point of a line haptic object that provides the desired trajectory. Once the tool center point is within the predefined distance of the starting point, actuation of an input causes the robotic arm to autonomously align and position the surgical tool on the desired trajectory. Once the surgical tool is in the desired position, the robotic system may effectively hold the rotational axis of the surgical tool on the desired trajectory by tracking movement of the patient and autonomously adjusting the robotic arm as needed to keep the rotational axis on the desired trajectory. Such teachings can be found in U.S. Patent Application Publication No. 2014/0180290 to Otto et al., filed on Dec. 21, 2012, entitled "Systems and Methods for Haptic Control of a Surgical Tool," which is hereby incorporated by reference herein in its entirety.

During operation of a robotic surgical system, the operation of the surgical tool can be modified based on comparing actual and commanded states of the tool relative to the surgical site is described in U.S. Patent Application Publication No. 2018/0168750 to Staunton et al., filed on Dec. 13, 2017, entitled Techniques for Modifying Tool Operation in a Surgical Robotic System Based on Comparing Actual and Commanded States of the Tool Relative to a Surgical Site," which is hereby incorporated by reference herein in its entirety. Further, robotic systems may be designed to respond to external forces applied to it during surgery, as described in U.S. Patent Application Publication No. 2017/0128136 to Post, filed on Nov. 3, 2016, entitled "Robotic System and Method for Backdriving the Same," which is hereby incorporated by reference herein in its entirety.

Further, because of the non-homogeneity of bone, applying a constant feed rate, a uniform tool path, and a constant rotational speed may not be efficient for all portions of bone. Systems and methods for controlling tools for such non-homogenous bone can be advantageous as described in U.S. Pat. No. 10,117,713 to Moctezuma de la Barrera et al., filed on Jun. 28, 2016, entitled "Robotic Systems and Methods for Controlling a Tool Removing Material From a Workpiece," which is hereby incorporated by reference herein in its entirety.

FIGS. 13-16 show a system 200 that includes a cannulated sleeve 240 and a drill bit 224. System 200 includes many similar features as system 100, except that system 200 utilizes a different lock assembly on cannulated sleeve 240. As discussed above, with reference to system 100, sleeve 240 includes burr extension 250 which may be manufactured as a single, monolithic piece or as two attachable pieces. The disclosure contemplates a kit including sleeve 240 and at least one burr extension 250. The kit may include a plurality of burr extensions 250 having different diameters to accommodate the anatomy and needs of a surgical procedure.

Figure 14:
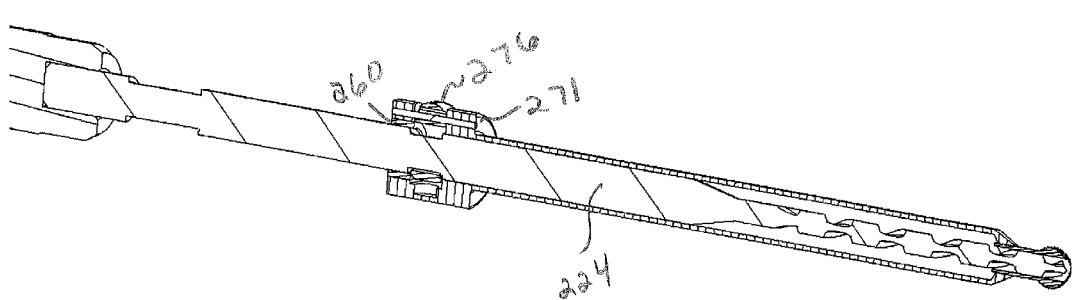
FIG. 14 is a cross-sectional view of the system of FIG. 13.
Figure 15:
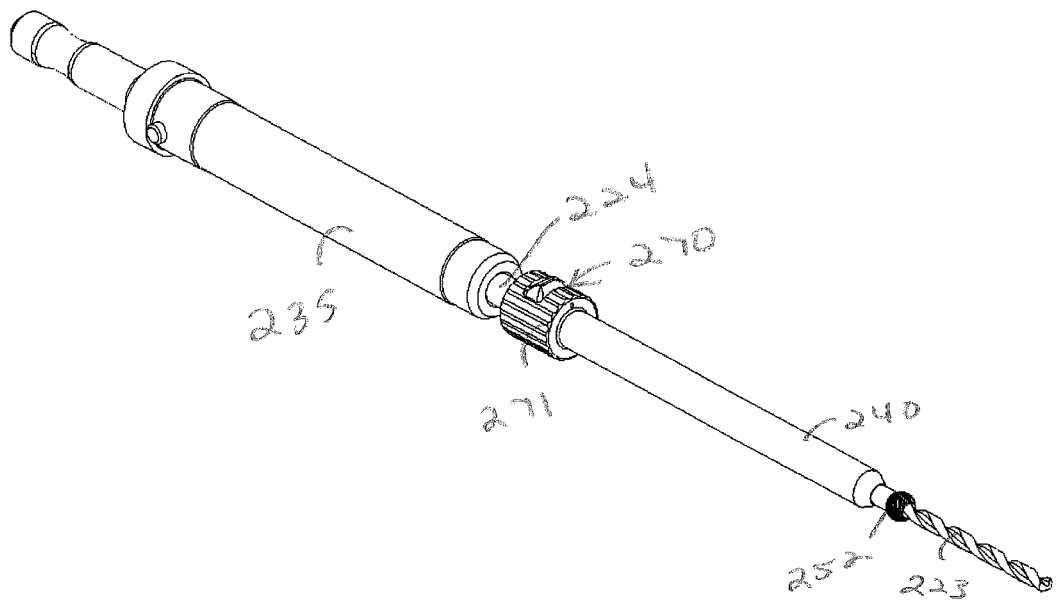
FIGS. 15 and 16 are a perspective side view and a cross-sectional view, respectively, of the system of FIG. 13 with the drill bit exposed at the distal end.
Figure 16:
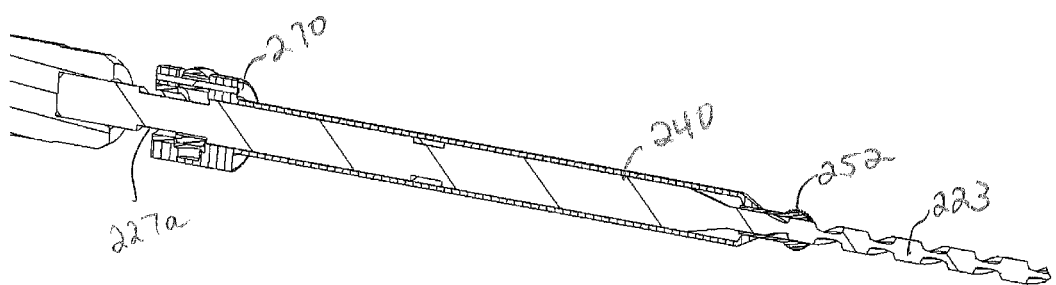
Figure 17:
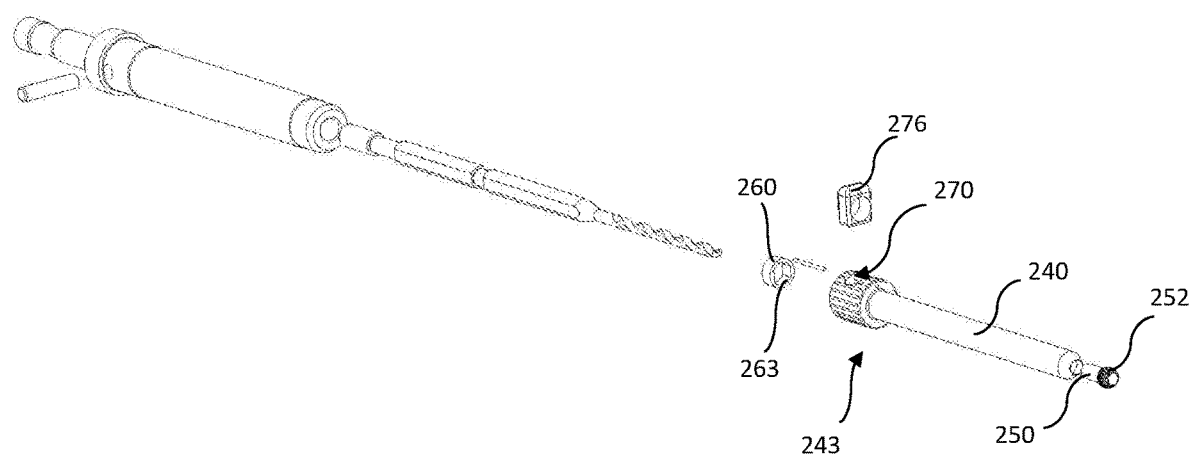
FIG. 17 is an exploded view of the system of FIG. 14.

Proximal end 243 of cannulated sleeve 240 includes lock assembly 270 for rotationally and axially coupling drill bit 224 and sleeve 240. Lock assembly 270 includes spring-loaded button 276 positioned within tubular member 271, and is substantially identical to button 176 of system 100. As shown in FIG. 17, ring 260 is attached, e.g. welded, to tubular member 271 and includes inner surface 263 that is keyed along a portion of the inner surface to mate with the keyed portion of drill bit 224 to rotatably couple the drill bit and sleeve 240 when lock assembly 270 is locked. In a rest condition, button 276 is biased by spring 280 so that the spring maintains secure engagement with drill bit 224. As shown in FIG. 14, button 276 engages reduced diameter segment 227b of drill bit 224 to lock the drill bit 224 relative to lock assembly 270 and to sleeve 240. Thus, in a locked configuration, with lock assembly 270 engaged, cannulated sleeve 240 is rotationally and axially locked with drill bit 224. In an actuated condition of button 276, when button 276 is depressed by a user, spring 280 is compressed and sleeve 240 is disengaged from drill bit 224 and can be moved along drill bit 224, as shown in FIG. 15. In this configuration, sleeve 240 is retracted such that keyed ring 260 is not rotationally locked with drill bit 224, but rather drill bit 224 can rotate for drilling and sleeve 240 can freely spin relative to the drill bit.

In use, system 200 is used in a similar manner to that described above with reference to system 100, as described with reference to FIGS. 8-12.

FIGS. 18-28 show system 300 according to another embodiment of the present disclosure. System 300 is similar in many respects to system 100 and is designed to facilitate co-axial burring and drilling of a target location of bone. The system forms a landing zone or pocket on the surface of the bone, e.g. a pedicle of a vertebra, to prevent the subsequent drill from skiving during hole preparation during surgery, e.g. spinal surgery. Generally, system 300 includes a burr tool disposed within a guide tube and rotated about an insertion axis to form a pocket on the surface of the bone. The burr tool is removed and the drilling tool is inserted within the guide tube and rotated about the insertion axis at the pocket to form the hole into which the implant will be inserted. Due to the pocket formed prior to drilling, the drill is prevented from skiving.

Figure 18:
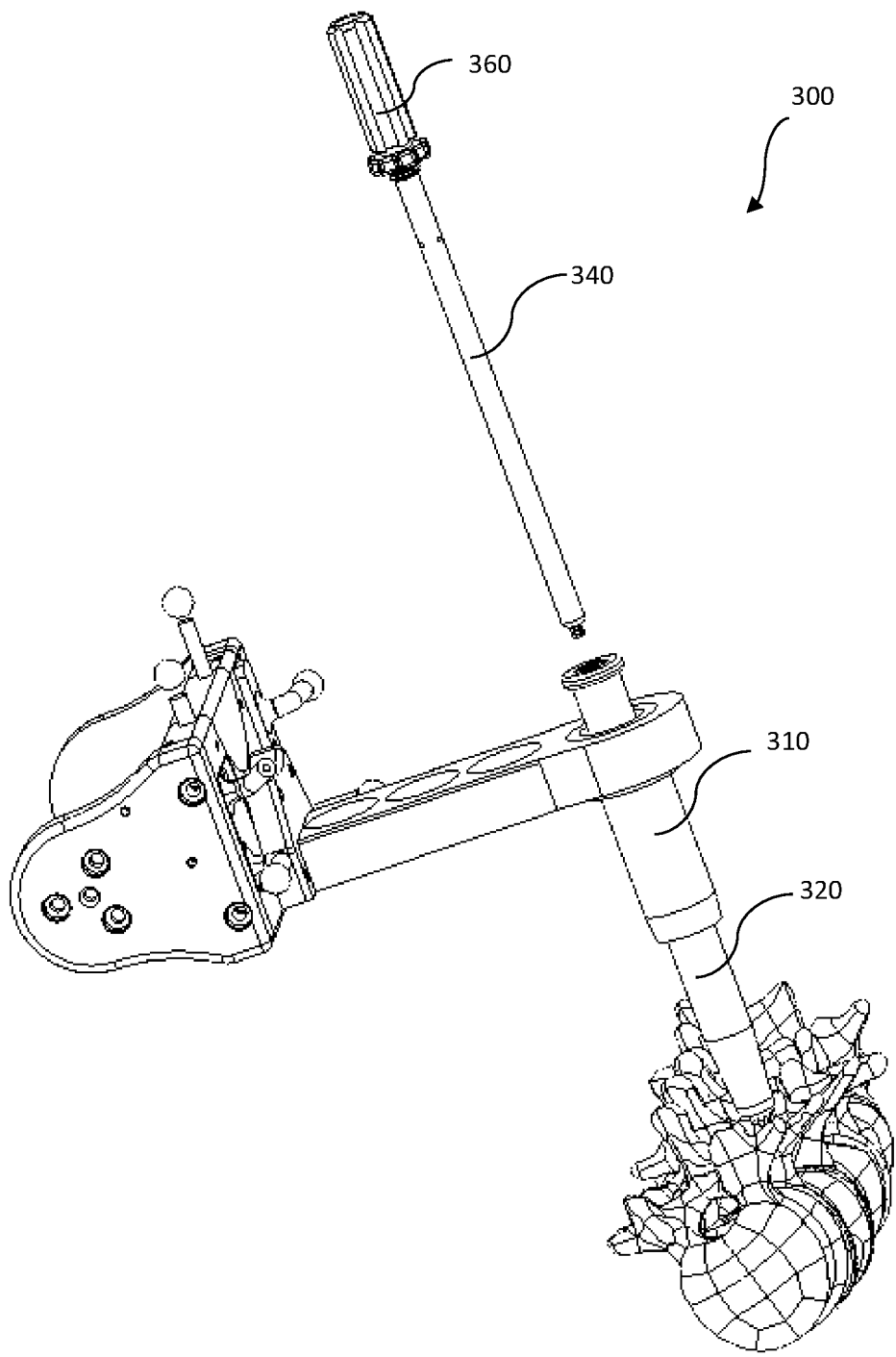
FIG. 18 is perspective side view of a system in accordance with another aspect of the present disclosure.
Figure 19:
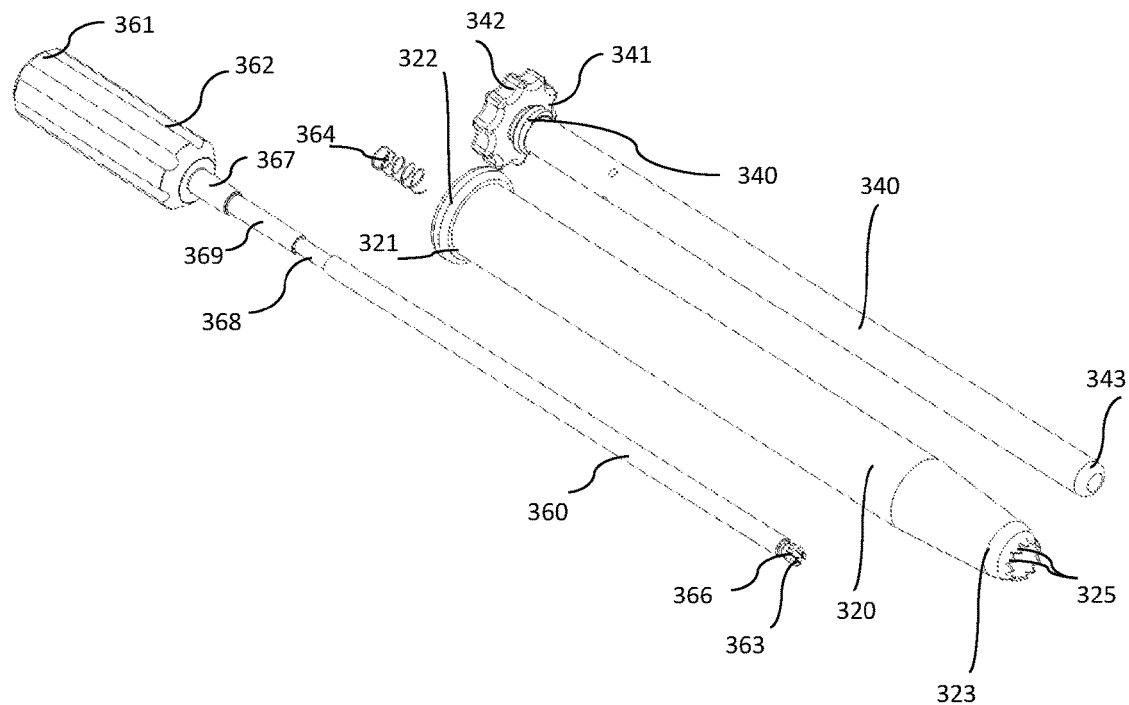
FIG. 19 is an exploded view of the system of FIG. 18.

System 300 is designed for robotic use, as shown with a robotic arm in FIG. 18 and cylindrical sleeve 310 through which system 300 is designed to fit. System 300 includes guide tube 320, obturator 340, burr 360 and drill 380. As shown in FIG. 19, guide tube 320 extends from proximal end 321 to distal end 323 and includes a cannulation through the length of the guide tube. Proximal end 321 includes collar 322 extending around the circumference of the guide tube 320. Distal end 323 includes teeth 325 extending around the circumference of the distal end. In the illustrated embodiment, teeth 325 are in the form of serrations each having a generally triangular shape such that each tooth terminates at a point. The teeth may be formed to allow for engagement with the bone to dock the guide tube. Although in other examples, the distal end may have a knife-edge or other known sharp edge which may facilitate engagement with the bone. Guide tube 320 is cylindrical along a substantial portion of the length and tapers inwardly at distal end 323.

Figure 21:
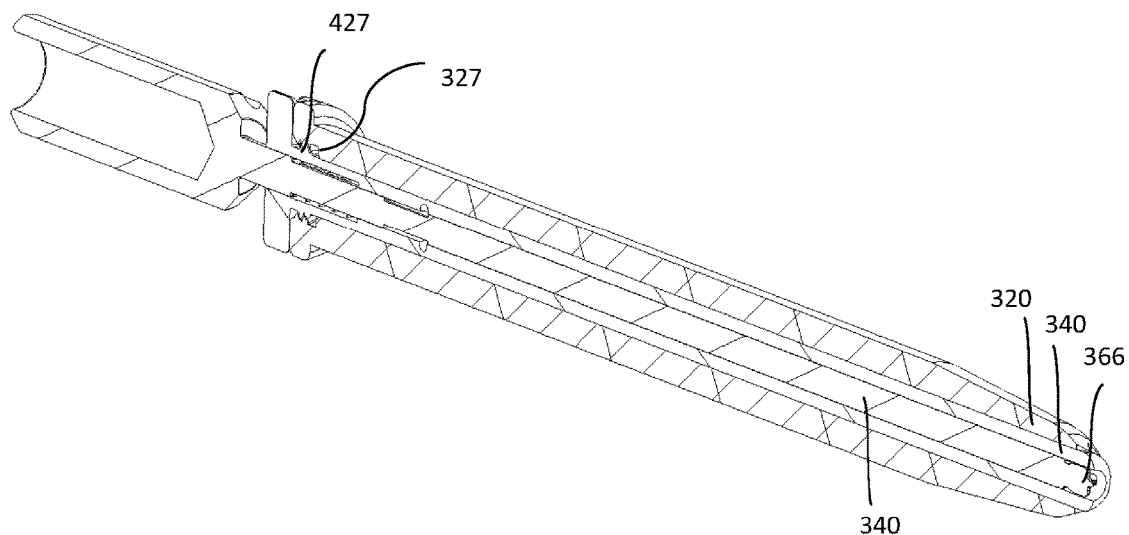

As discussed above, guide tube 320 has an outer diameter sized to fit within sleeve 310 of the robotic system 300. The inner diameter of guide tube 320 is sized to receive obturator 340 and the burr 360 within the obturator. Additionally, with the obturator 340 and burr 360 removed from the guide tube 320, a drill is receivable within the cannulation of the guide tube. An inner surface of guide tube 320 includes threaded portion 327 at proximal end 321 for threaded engagement with an outer surface of obturator 340, as shown in FIG. 21.

Figure 20:
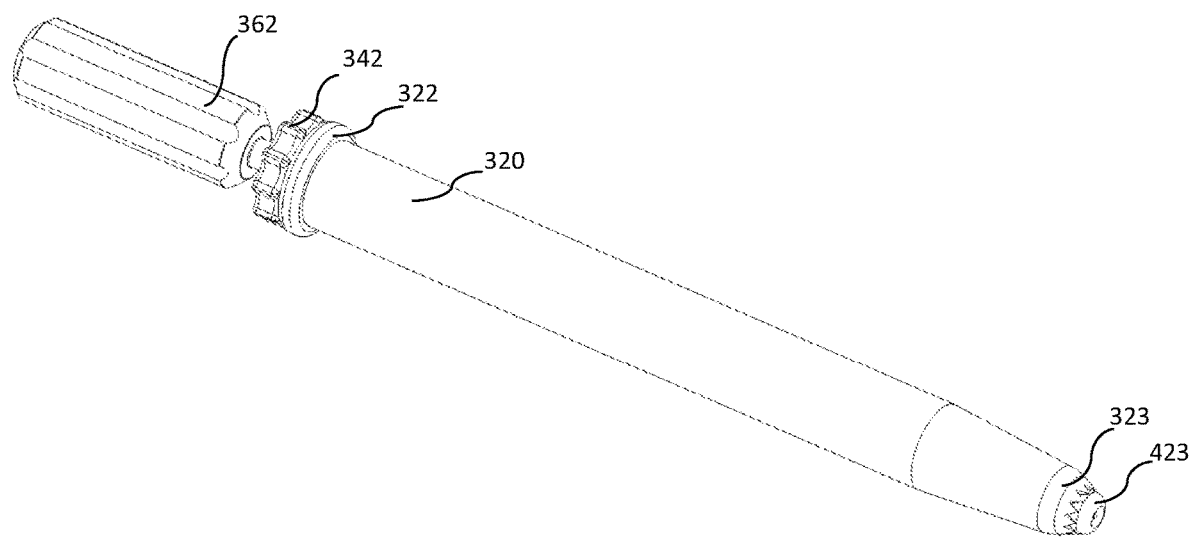
FIGS. 20 and 21 are a perspective side view and a cross-sectional view, respectively, with the burr tip within the guide of the system of FIG. 18.

FIG. 19 shows obturator 340 which has a smooth outer surface to reduce trauma to the soft tissue during surgery. Obturator 340 is sized to fit within and coaxial with guide tube 320. Obturator 340 has a generally cylindrical shape and is cannulated to receive burr 360 coaxial with the obturator. Obturator 340 extends between proximal end 341 and distal end 343. At proximal end 341, the outer surface includes threaded portion 347 corresponding to internal threaded portion 327 of guide tube 320, shown in FIG. 21. Additionally, proximal end 341 includes cap 342 that has a diameter greater than the body of the obturator. As shown in FIG. 20, collar 322 of guide tube 320 and cap 342 of obturator 340 may have substantially equal diameters, and cap 342 is configured to proximally abut the collar of the guide tube. Distal end 343 is generally rounded to avoid trauma to soft tissue as the obturator moves through the soft tissue.

Burr 360 is spring-loaded into obturator 340. Burr 360 extends between proximal end 361 and distal end 363. Proximal end 361 includes handle 362 for controlling rotation of the burr tool. Distal end 363 includes burr tip 366 for cutting the bone to create a pocket within the bone to prevent skiving of the drill during the drilling of a hole. Burr tip 366 includes cutting elements 370 positioned around the circumference of the burr tip with a sharp pointed tip 371, best shown in FIG. 24. The cutting elements 370 are convexly shaped separated from one another by concave surfaces around the circumference. From a bottom profile, the burr tip 366 has a substantially X shape.

Figure 23:
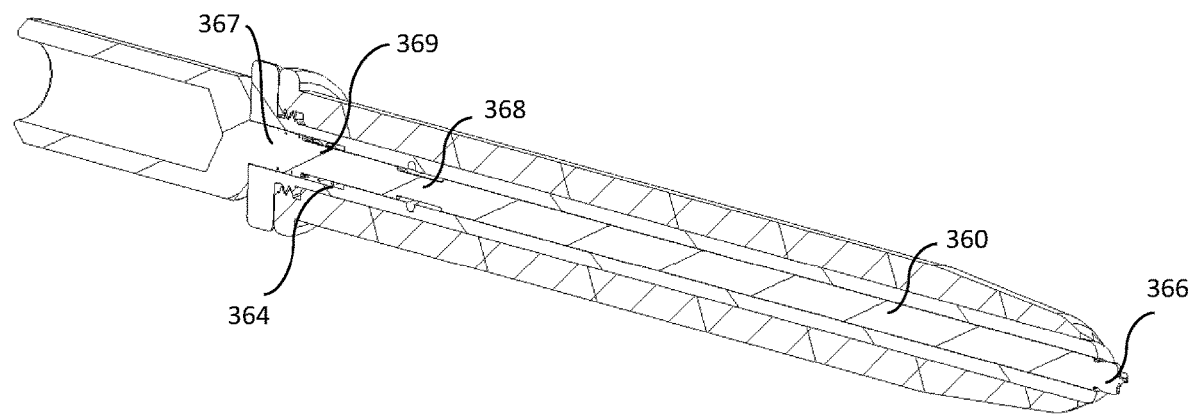
Figure 24:
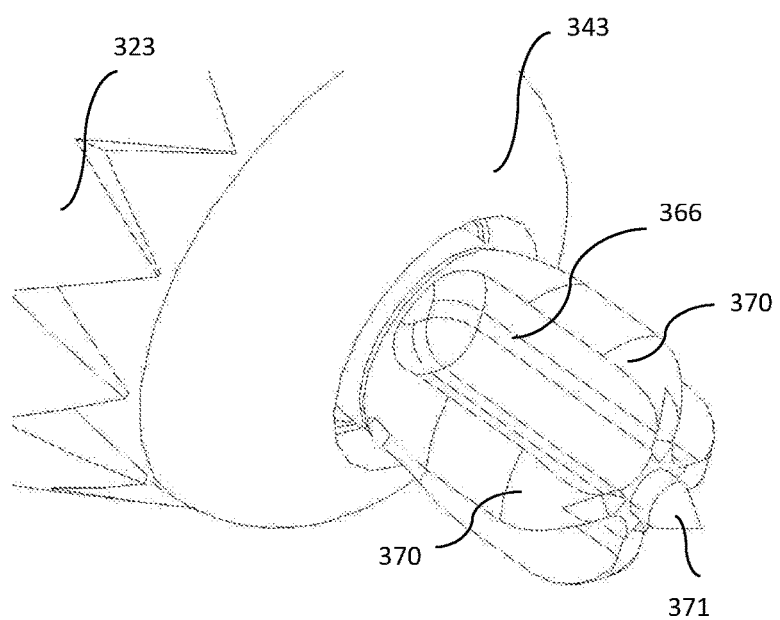
FIG. 24 is an enlarged view of a burr tip of a burr tool of the system of FIG. 18.

Burr 360 includes a larger diameter portion 367 adjacent handle 362 and a reduced diameter portion 368 separated from one another by engagement portion 369, as shown in FIG. 19. Spring 364 is positioned around engagement portion 369 and the burr may be pinned to obturator 360 at a position along reduced diameter portion 368, as shown in FIG. 23.

Figure 22:
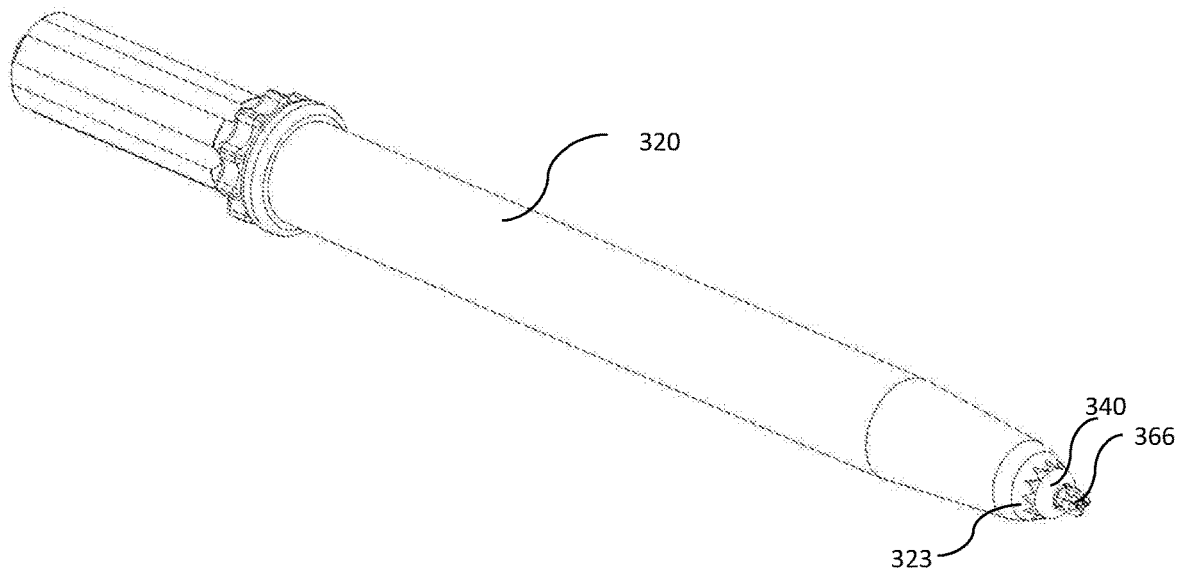
FIGS. 22 and 23 are a perspective side view and a cross-sectional view, respectively, of the system of FIG. 18 with the burr tip exposed at the distal end.

Burr 360 is first spring-loaded into the obturator 340, as shown in FIG. 19, and then the obturator (with the burr therein) is loaded into guide tube 320 via the corresponding threaded portions of the obturator and the guide tube. When loaded into guide tube 320, the guide tube, obturator 340 and burr 360 are all coaxial. Spring 364 allows for burr 360 to move slightly axially to allow the burr to move from a first, proximal position in which burr tip 366 is within the guide tube 320 and/or obturator 340, as shown in FIGS. 20 and 21, to a second, distal position in which burr tip 366 is exposed and distal to the obturator and guide tube, as shown in FIGS. 22 and 23. Further, burr 360 is rotatable in order to cut the bone to form the pocket.

Figure 25:
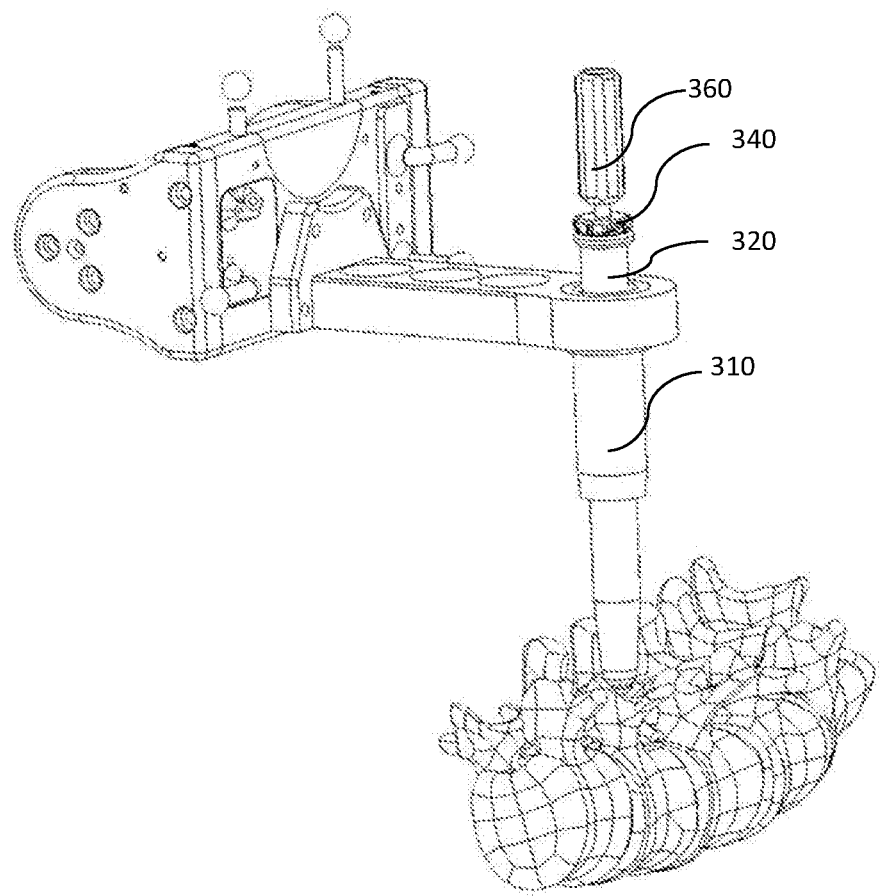
FIG. 25 is a schematic view of the system of claim 18 adjacent the pedicle.
Figure 26:
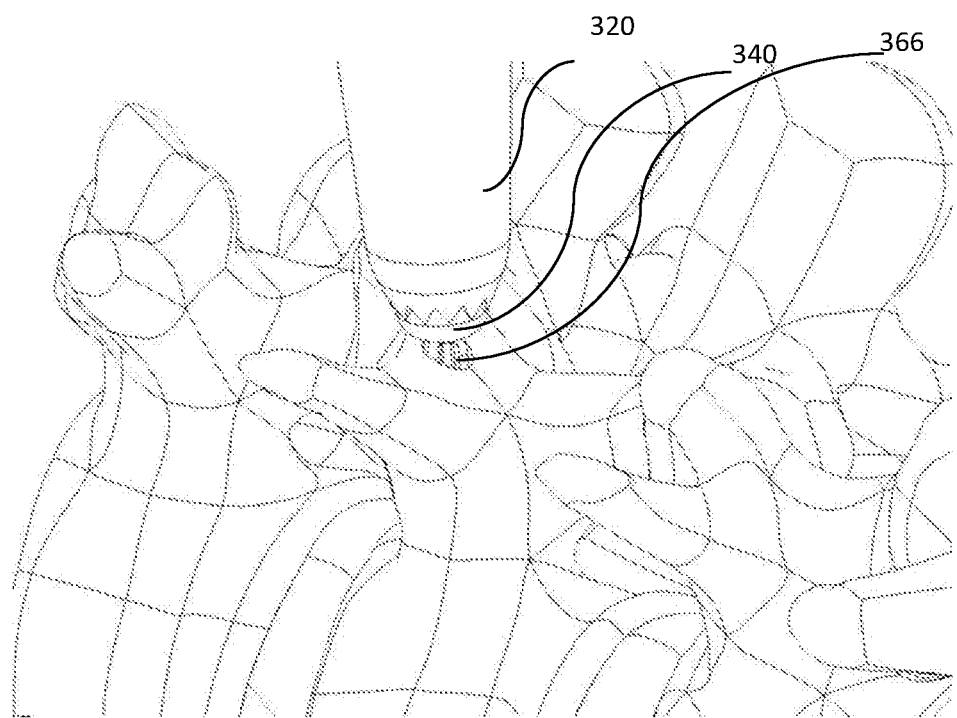
FIG. 26 is an enlarged schematic view of the burr tip of the burr tool of the system of FIG. 18 at the pedicle.

As shown in FIG. 25, the system 300 including the burr 360, obturator 340 and guide tube 320, is loaded into sleeve 310 and the robotic arm along an insertion axis and positioned against the pedicle bone. Burr 360 is rotated about the insertion axis to form the pocket in the pedicle bone, in which the drill or drill bit will subsequently be positioned and drilled. The pocket is formed within a bone surface that is not perpendicular to the insertion axis, as discussed above with reference to system 100. The pocket is a shallow pocket with a substantially rounded surface which prevents skiving of the drill when the drill is positioned at the pocket.

Figure 27:
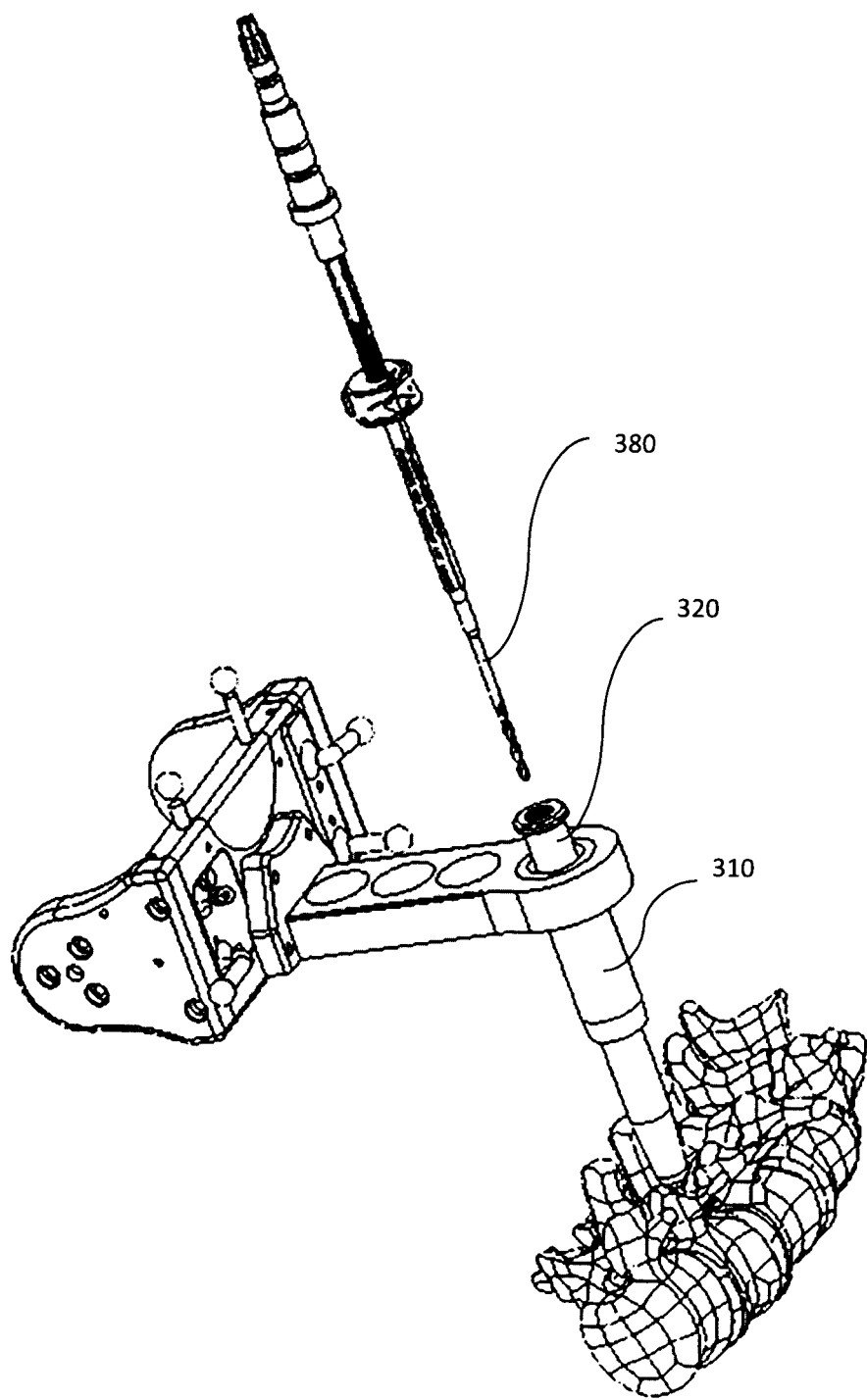
FIG. 27 is a perspective side view of a drill used in conjunction with the system FIG. 18.
Figure 28:
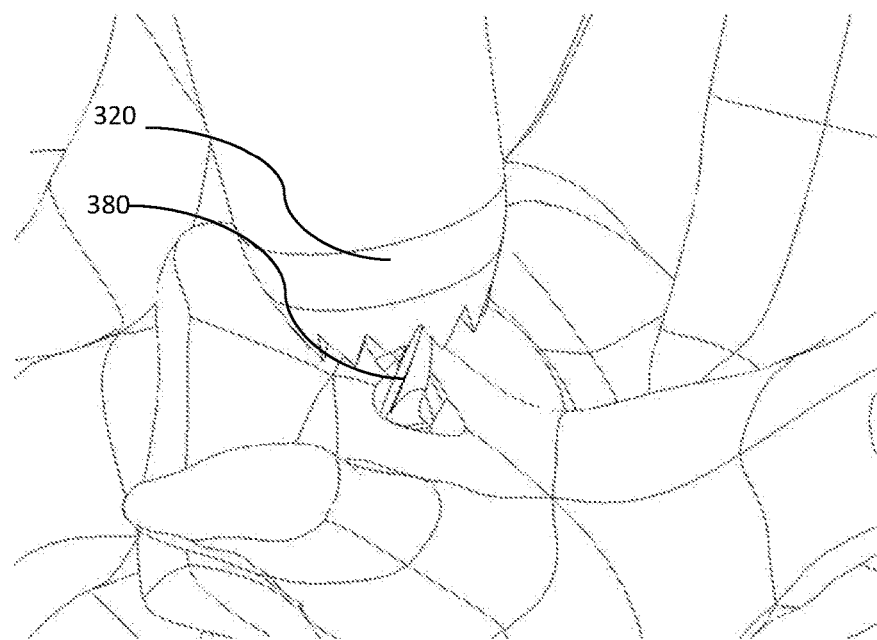
FIG. 28 is a schematic view of the system of FIG. 18 drilling into the pedicle.

After the pocket is formed, the obturator 340 and burr 360 are removed distally from the guide tube 320 and the drill 380 is placed within the guide tube, shown in FIG. 27. Drill 380 is rotatably keyed to the guide tube 320 to rotationally lock them together such that the drill and thus guide tube are rotated at the pocket. The rotation of the drill causes formation of the hole within the pocket, as shown in FIG. 28. An implant, such as a pedicle screw, may be implanted within the hole.

Figure 29:
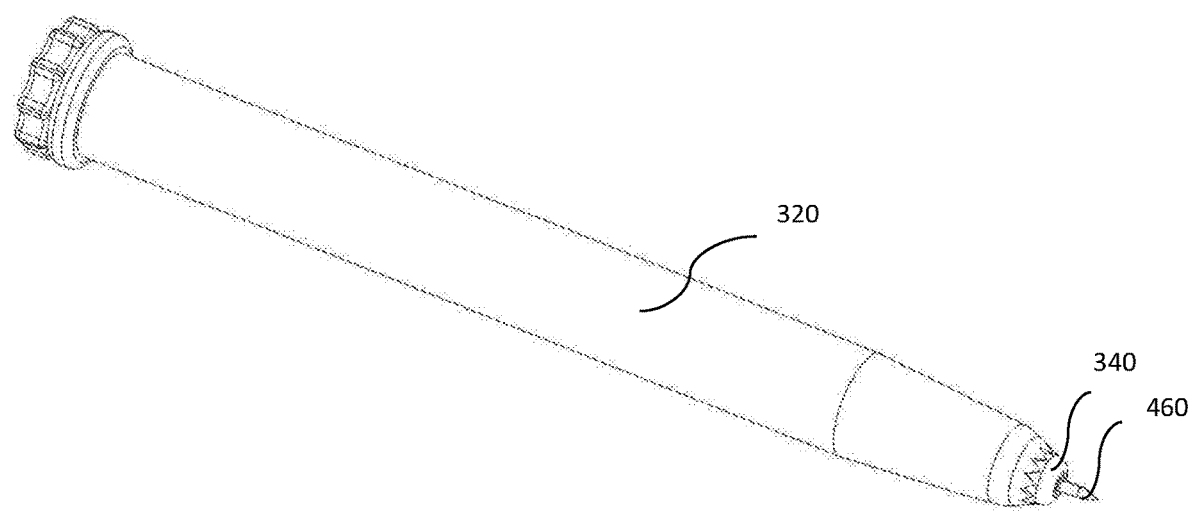
FIGS. 29 and 30 are a perspective side view and a cross-sectional view, respectively, of a system in accordance with an alternative aspect of the present disclosure.
Figure 30:
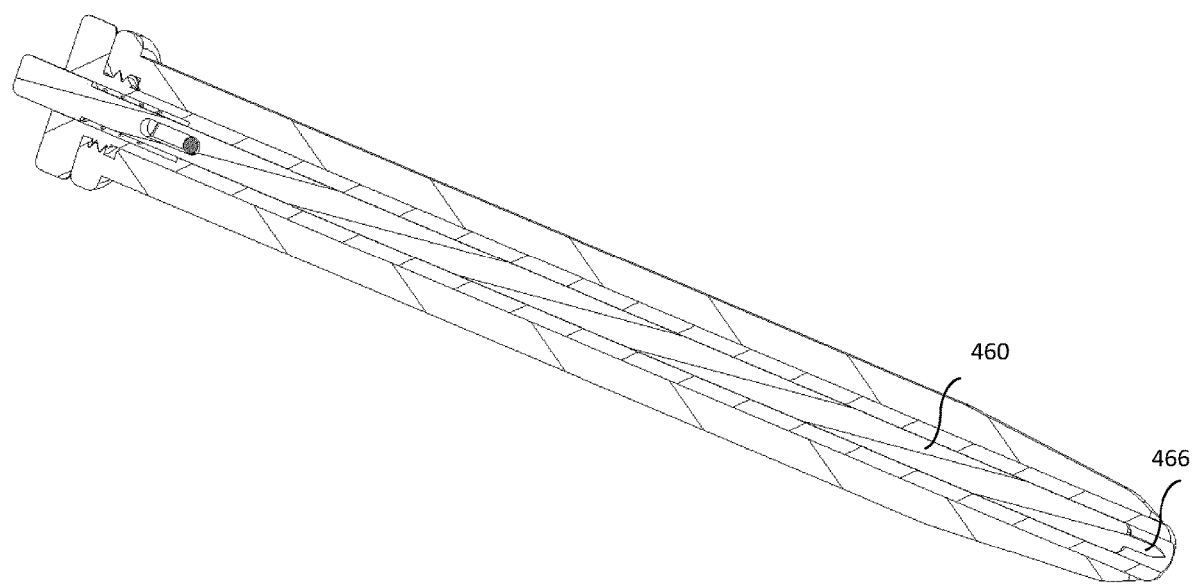

In an alternative embodiment, shown in FIGS. 29 and 30, the guide tube 320 and obturator 340 are used in conjunction with a spring-loaded awl 460 rather than burr 360. Awl 460 includes a pointed tip 466 for engaging the bone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrange-

The invention claimed is:

1. A system to prevent skiving at an implant insertion site on a bone, the system comprising:
   a surgical tool including a cannulated sleeve having a distal end defining a burr surface; and
   a drill bit configured to be disposed within the cannulated sleeve,
   wherein in a first configuration the cannulated sleeve and the drill bit are rotationally coupled to each other and in a second configuration the cannulated sleeve and the drill bit rotate independent of one another.

2. The system of claim 1, wherein the burr surface is annular.

3. The system of claim 1, wherein the burr surface is bulbous.

4. The system of claim 1, wherein the distal end is detachable from the cannulated sleeve.

5. The system of claim 1, wherein the distal end and the cannulated sleeve are of a single monolithic construction.

6. A kit comprising:
   the system of claim 4; and
   more than one distal end, each of the distal ends defining a burr surface having a different cutting surface from the others.

7. The system of claim 1, wherein the cannulated sleeve has a lock at the proximal end of the cannulated sleeve to axially and rotationally couple the cannulated sleeve and the drill bit.

8. The system of claim 1, wherein the system is configured to be actuated by a robotic end effector.

9. The system of claim 1, wherein the distal end of the cannulated sleeve defines an opening.

10. A system to prevent skiving at an implant insertion site on a bone, the system comprising:
    a surgical tool including a cannulated sleeve having a distal end defining a burr surface; and
    a drill bit configured to be disposed within the cannulated sleeve,
    wherein the cannulated sleeve has a lock at the proximal end of the cannulated sleeve to rotationally couple the cannulated sleeve and the drill bit.

11. The system of claim 10, wherein the burr surface is annular.

12. The system of claim 10, wherein the burr surface is bulbous.

13. The system of claim 10, wherein the distal end is detachable from the cannulated sleeve.

14. The system of claim 10, wherein the distal end and the cannulated sleeve are of a single monolithic construction.

15. A kit comprising:
    the system of claim 13; and
    more than one distal end, each of the distal ends defining a burr surface having a different cutting surface from the others.

16. The system of claim 10, wherein the system is configured to be actuated by a robotic end effector.

17. The system of claim 10, wherein the distal end of the cannulated sleeve defines an opening.

18. A surgical system for use with a drill bit to prevent skiving at an implant insertion site on a bone, the system comprising:
    a cannulated guide tube;
    an obturator configured to be disposed within the guide tube; and
    a burr tool configured to be disposed within the obturator, the burr tool having a distal end defining a burr surface.

19. The surgical system of claim 18, wherein the guide tube, obturator, and burr tool are coaxial when the obturator is positioned in the guide tube and the burr tool is positioned in the obturator.

20. The surgical system of claim 18, further comprising a drill bit configured to be disposed within the guide tube.

* * * * *